(12) United States Patent
Goldsborough

(10) Patent No.: US 7,790,373 B2
(45) Date of Patent: Sep. 7, 2010

(54) CLEAN-UP BEADS

(75) Inventor: Andrew S. Goldsborough, St. Gely du Fesc (FR)

(73) Assignee: Cyclops Genome Sciences Limited, Cambridge (GB)

( * ) Notice: Subject to any disclaimer, the term of this patent is extended or adjusted under 35 U.S.C. 154(b) by 592 days.

(21) Appl. No.: 10/565,694

(22) PCT Filed: Jul. 23, 2004

(86) PCT No.: PCT/GB2004/003201

§ 371 (c)(1),
(2), (4) Date: Mar. 24, 2008

(87) PCT Pub. No.: WO2005/012522

PCT Pub. Date: Feb. 10, 2005

(65) Prior Publication Data

US 2008/0220413 A1    Sep. 11, 2008

(30) Foreign Application Priority Data

Jul. 23, 2003 (GB) ................................. 0317199.8
Aug. 19, 2003 (GB) ................................. 0319422.2

(51) Int. Cl.
*C12Q 1/68* (2006.01)
(52) U.S. Cl. .......................................... 435/6; 435/975
(58) Field of Classification Search .................. None
See application file for complete search history.

(56) References Cited

U.S. PATENT DOCUMENTS

| 6,794,140 B1 | 9/2004 | Goldsborough |
| 6,867,290 B2 | 3/2005 | Goldsborough |
| 2005/0074753 A1 | 4/2005 | Goldsborough |
| 2005/0272679 A1 | 12/2005 | Goldsborough |
| 2006/0147918 A1 | 7/2006 | Goldsborough |

FOREIGN PATENT DOCUMENTS

| JP | 2000327315 A | * 11/2000 |
| WO | WO 90/10637 A1 | 9/1990 |
| WO | WO 00/66605 | 11/2000 |

(Continued)

OTHER PUBLICATIONS

Baker A D et al: "Enantiomeric Resolution of Tris-I IO-Phenanthrolineruthenium Ion and BIS-2 2'-Bipyridineruthenium 4'7'-Phenanthrolino-5'6'5 6-Pyrazine Ion on a DNA Hydroxylapatite Column" Journal of the American Chemical Society, vol. 113, No. 4, 1991, pp. 1411-1412.*

(Continued)

*Primary Examiner*—Christopher M. Babic
(74) *Attorney, Agent, or Firm*—Saliwanchik, Lloyd & Saliwanchik

(57) ABSTRACT

The present invention provides a material for separating an analyte from an undesired constituent, which material comprises a solid phase and a coating, wherein the solid phase is capable of binding the undesired constituent, and wherein the coating covers the exposed surface of the solid phase to an extent that any binding of the solid phase to the analyte is impeded. A method for preparing the material, and uses of the material for separating an analyte from an undesired constituent are also provided.

37 Claims, 2 Drawing Sheets

FOREIGN PATENT DOCUMENTS

Figure 1:
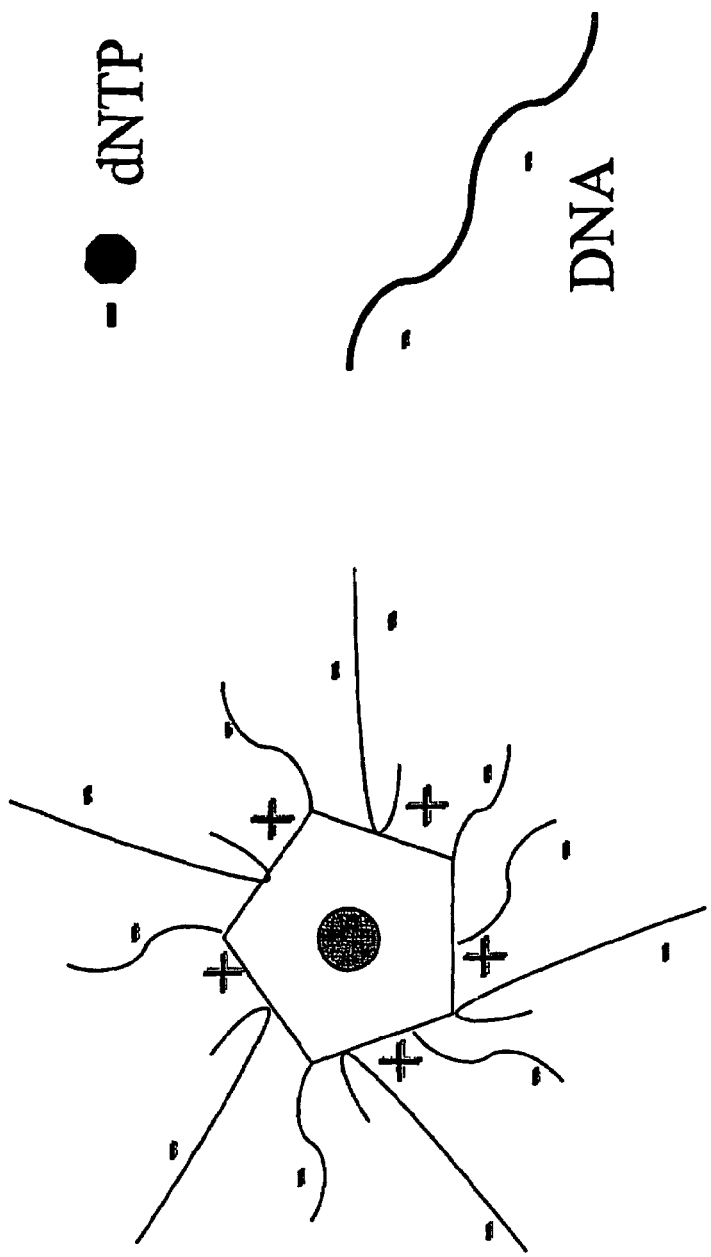

| WO | WO 00/75302 A2 | 12/2000 |
|----|----|----|
| WO | WO 00/75306 | 12/2000 |
| WO | WO 0173123 A2 * | 10/2001 |
| WO | WO 01/94626 | 12/2001 |
| WO | WO 2004/013155 A2 | 2/2004 |

OTHER PUBLICATIONS

Aldrich-Wright, J. R. et al. "Development of DNA-immobilised chromatographic stationary phases for optical resolution and DNA-affinity comparison of metal complexes" *Journal of Chromatography A*, Dec. 22, 1995, pp. 436-443, vol. 178, No. 2.

Baker, A. D. et al. "Enantiomeric Resolution of $Ru(phen)_3^{2+}$ and $Ru(bpy)_2ppz^{2+}$ on a DNA-Hydroxylapatite Column" *Journal of American Chemical Society*, 1991, pp. 1411-1412, vol. 113, No. 4.

Labrou, N. et al. "The affinity technology in downstream processing" *Journal of Biotechnology*, Aug. 15, 1994, pp. 95-119, vol. 36, No. 2.

Roe, S. "5. Separation on the Basis of Charge" In: *Protein Purification Methods A Practical Approach*, Edited by E.L.V. Harris and S. Angal, 1989, pp. 200-201, Oxford University Press, New York.

Slater, R.J. "The Purification of Poly(A)-Containing RNA by Affinity Chromatography" In: *Methods in Molecular Biology*, Edited by John M. Walker, 1984, pp. 117-120, vol. 2, Nucleic Acids, Humana Press, Clifton New Jersey.

* cited by examiner

CLEAN-UP BEADS

CROSS-REFERENCE TO RELATED APPLICATION

This application is the U.S. national stage application of International Patent Application No. PCT/GB2004/003201, filed Jul. 23, 2004, the disclosure of which is hereby incorporated by reference in its entirety, including all figures, tables and amino acid or nucleic acid sequences.

Described is a means to differentially separate molecules based on one or more of the molecules' physical properties such as charge and/or size. Separation occurs by means of a surface treatment of a solid phase where the surface treatment forms a separation between the solid phase and the sample. The solid phase has the capacity to bind one or more of the constituents contained in the sample thereby removing one or more undesired constituents such as a contaminant from the analyte. The solid phase, without any surface treatment, is capable of binding to the undesired constituent. Typically, the solid phase, without any surface treatment, is also capable of binding both the undesired constituent and the analyte so that no separation occurs. In such cases, the ability of the solid phase to differentially bind either the analyte or contaminant is dependent on the properties of the surface treatment.

The surface treatment provides a selective barrier for the constituents of the analyte solution to the solid phase. The selectivity is based on the ability of the surface treatment to exclude molecules of a certain size and/or charge from the underlying solid phase. For example, it has surprisingly been found that a polynucleotide surface treatment of hydroxylapatite particles provides a semi-permeable barrier to a mixture of labelled nucleotides and a labelled polynucleotide, whereby the nucleotides are bound by the underlying solid phase because of their relatively small size compared with the polynucleotide. The exclusion of the analyte polynucleotide from the underlying solid phase is based on charge repulsion, binding competition and/or size exclusion by the surface treatment. In this example the unwanted labelled nucleotides can be removed from the desired labelled polynucleotide and the invention provides an efficient means, for example, to remove unincorporated labelled nucleotides from the desired labelled polynucleotide following a labelling reaction (Sambrook et al., (1989) Molecular Cloning: A Laboratory Manual, CSH).

Automated high throughput sequencing requires the essential step of removing salts and unincorporated dye labelled terminators from the desired reaction products. Current methods to remove nucleotides from polynucleotides require lengthy and sometimes costly processes, in particular gel filtration with for example, Sephadex G-10, G-25, G-50 or G-75 (Amersham Biosciences, UK). This method necessitates the pre-swelling of Sephadex beads, pouring a column, replenishment of column buffer and the collection of several fractions in order to determine the fraction containing the desired polynucleotide. Gel filtration of radioactive samples can expose the operator to significant radioactive exposure for substantial periods. Other gel filtration methods make use of spin columns that can be used in centrifuges, which although faster than the use of columns still requires considerable operator hands on time. Gel filtration methods are poorly adapted to automation because they require many centrifugation or vacuum drying steps. Likewise, ethanol precipitation, another commonly used method for the removal, for example, of nucleotides from a polynucleotide is a lengthy and inefficient method that frequently results in substantial sample loss and salt contamination and is not suitable for automation.

The present invention improves on the separation methods known in the art, by providing a rapid method for separating an analyte from an undesired constituent. Advantageously, in this method, the analyte remains in solution, eliminating the need for elution or recovery steps that are expensive or result in loss of the analyte.

In a first aspect, the invention provides a material for separating an analyte from an undesired constituent, which material comprises a solid phase and a coating, wherein the solid phase is capable of binding the undesired constituent, and wherein the coating covers the exposed surface of the solid phase to an extent that any binding of the solid phase to the analyte is impeded.

Typically, the solid phase is capable of binding the analyte in the absence of coating. The coating therefore impedes the binding of the solid phase to the analyte. In other words, the binding of the analyte to the solid phase is reduced by the presence of the coating. The degree to which binding is impeded may be determined by measuring the binding of the analyte to the solid phase in the presence and absence of coating.

In one embodiment, the solid phase and coating are selected such that more than 50% undesired constituent is capable of binding the solid phase of the material. It is preferred that more than more than 75%, or more than 90% of the undesired constituent is capable of binding the solid phase. In one embodiment, less than 50% of the analyte is capable of binding the solid phase. It is preferred that less than 25%, or less than 10% of the analyte is capable of binding the solid phase.

The solid phase and coating are selected such that the material is capable of selectively binding an undesired constituent from a sample containing an undesired constituent and desired analyte.

The solid phase must be capable of binding the undesired constituent. The skilled person will be able to identify suitable solid phases for binding to particular undesired constituents. The binding of the undesired constituent to the solid phase may take place by adsorption, absorption, charge, hydrophobicity, affinity, hydrogen bonding or covalent bonding.

Where the undesired constituent is charged, a solid phase having an opposite charge may be selected. This results in the undesired constituent binding the solid phase by electrostatic attraction.

Where the undesired constituent is a chelator, a solid phase capable of binding a chelator may be selected. Typically, a solid phase capable of binding a chelator comprises cations, such as metal ions, to which the chelator binds.

In embodiments in which the solid phase is capable of binding the analyte in the absence of coating, a coating must be selected that impedes the binding of the analyte whilst permitting the undesired constituent to bind. The skilled person is capable of selecting suitable coatings for this purpose. The coating usually impedes binding of the analyte by electrostatic repulsion and/or steric hindrance.

Where the analyte is charged, the coating may bear the same charge. Consequently, the coating repels the analyte and prevents this from binding the solid phase of the material of the invention. Where the analyte is larger than the undesired constituent, the coating may sterically block the analyte.

In a further aspect, the invention provides a method for preparing the material of the invention. The method comprises a step of contacting a solid phase with a surface treatment material to form a coating. Optionally, the method also comprises a step of isolating the material produced.

In a further aspect, the invention provides a method for separating an analyte from an undesired constituent. The method comprises contacting a sample containing the analyte and undesired constituent with the material of the invention under conditions that allow the undesired constituent to bind to the solid phase of the material, and optionally separating the sample containing the analyte from the material. The sample must be present in the gas or liquid phase.

In a preferred embodiment, at least 50% of the undesired constituent binds the solid phase of the material. It is preferred that more than more than 75%, or more than 90% of the undesired constituent binds the solid phase. In one embodiment, less than 50% analyte binds the solid phase. It is preferred that less than 25%, or less than 10% of the analyte binds the solid phase.

In one embodiment, the "undesired" constituent is eluted from the solid phase of the material and recovered.

In another embodiment, where the undesired constituent is labelled, the material recovered from the sample is assayed to determine the amount of undesired constituent bound. The amount of undesired constituent may be determined by assaying the label attached to the undesired constituent.

In a further aspect, the invention provides a kit for separating an analyte from an undesired constituent. The kit comprises the material of the invention. The kit additionally comprises at least one of the following components:
 a) a means for separating the material from a liquid or gaseous sample;
 b) a wash buffer that does not elute the undesired constituent from the material, but is capable of eluting the analyte from the material;
 c) sterile tubes or vessels;
 d) components to carry out a DNA or RNA labelling reaction; and
 e) a control for testing the ability of the material to bind to the undesired constituent.

The control for testing the ability of the material of the invention to bind to the undesired constituent typically comprises a labelled undesired constituent. The binding of this labelled undesired constituent to the material may be followed by measuring the removal of the labelled undesired constituent from a sample surrounding the material of the invention. Typically, coloured undesired constituents are used so that the efficacy of the material can be visually assessed, or measured with a colorimeter/spectrophotometer. However, the control may also be labelled with a radiolabel, an affinity label, an enzymatic label or a fluorescent label.

The invention will now be explained further with reference to the following figures:

FIG. 1 is a schematic diagram showing the distribution of charges present on a bead representing a material of the invention. The solid phase is positively charged and the coating is negatively charged.

Figure 2:
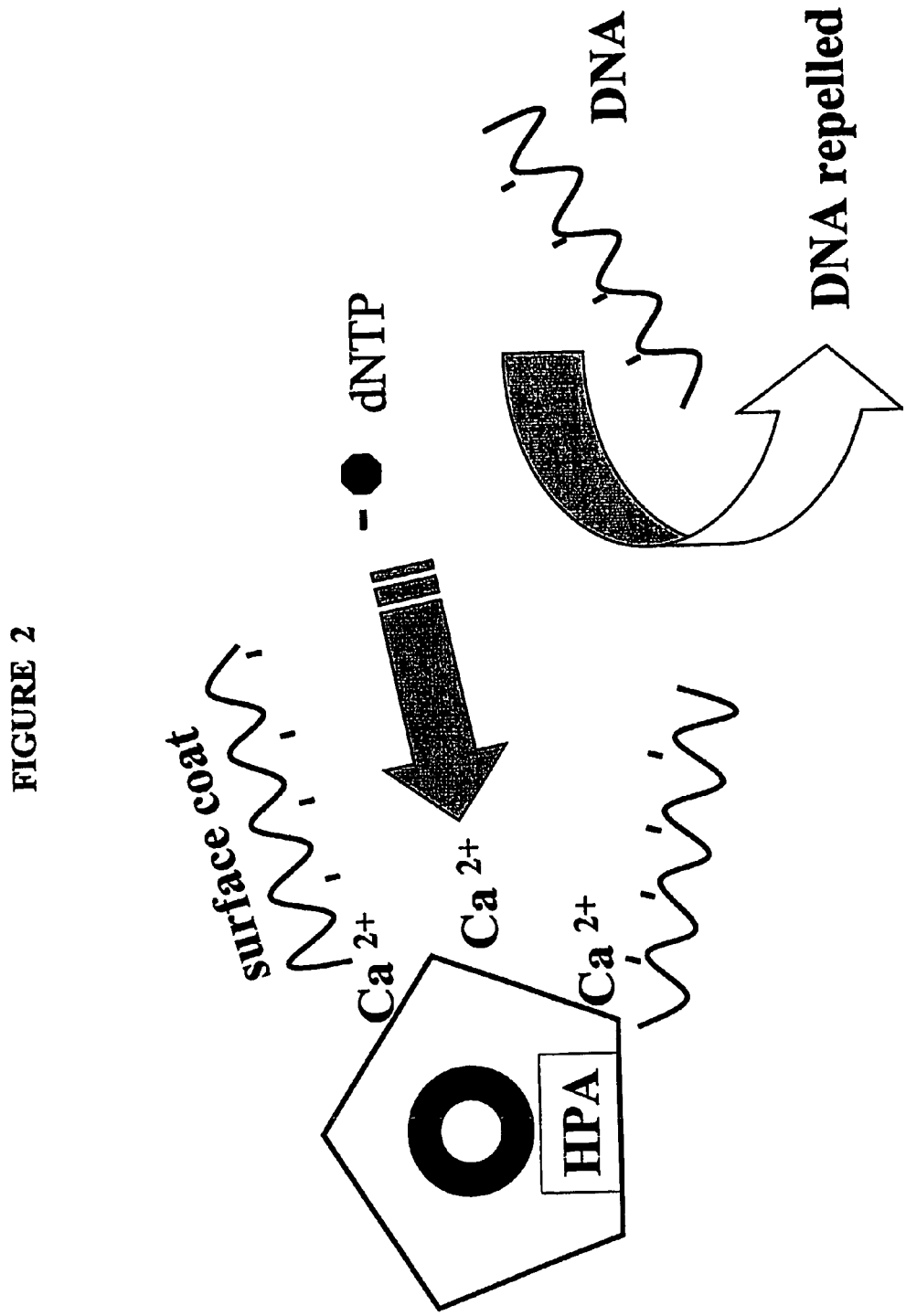

FIG. 2 is a schematic diagram showing how a bead comprising a hydroxylapatite (HPA) solid phase and polynucleotide coating may be used to separate dNTPs from DNA. The negatively charged DNA is electrostatically and sterically repelled by the polynucleotide coating. The dNTP is able to pass through the coat to bind the $Ca^{2+}$ ions of the hydroxylapatite solid phase.

In one embodiment of the invention, the undesired constituent such as unincorporated nucleotides are removed and trapped by the solid phase whilst the desired analyte such as DNA remains in solution. Current methods such as silica particle separation of nucleotides and polynucleotides requires the binding of the analyte to the solid phase followed by washing of the particles to remove the undesired constituent, followed finally by elution of the analyte from the solid phase. One of the advantages of this invention is that there is no elution step required because the solid phase binds only those components of the reaction which are non-desired leaving the purified analyte free in solution.

The analyte can be a (i) a polynucleotide such as single or double stranded DNA or RNA such as those derived from a polymerisation reaction such as reverse transcription, PCR, a DNA sequencing reaction, a labelling reaction such as nick translation or random priming, a product of RNA polymerisation reaction such as an in vitro transcription reaction (Sambrook et al., (1989) Molecular Cloning: A Laboratory Manual, CSH), (ii) a protein such as an enzyme, a cofactor, a receptor, a glycoprotein, an antibody, a phosphoprotein, an antigen, a diagnostic biomarker or (iii) a small drug like molecule such as a peptide, a steroid or cAMP.

The undesired constituent to be removed from the analyte can be one or more of the following (i) an unincorporated ribonucleotide, deoxyribonucleotide or dideoxyribonucleotide mono/di/ or triphosphate (also referred to as 'free-nucleotides') such as an unlabelled or fluorescently labelled nucleotide such as Cy5 or Cy3 CyDye™ (Amersham Pharmacia Biosciences, UK), rhodamine, fluorescein, TAMRA, 6-FAM, TET, Texas Red, Digoxigenine, Dabcyl, TaqMan Probes™, ATTO590, JOE, ROX, coumarin, or biotin, or cholesterol, or aminoallyl labelled or a 3H, 14C, 35S, 33P or 32P radioactively labelled nucleotide mono/di or triphosphate or labelled or non-labelled dideoxynucleotides, (ii) a salt such as CoCl2, CaCl2, LiCl2, MnCl2, MgCl2, KCl, NaCl, (NH4)2SO4 or sodium phosphate, (iii) a detergent such as SDS or SLS, (iv) a precursor such as tritium labelled thymidine, a labelled amino acid such as 35S cysteine or methionine, or 14C glycine, biotinylated lysine, fluorescently labelled lysine, a sugar such as 14C glucose phosphate, or 14C galactose, or phosphorous 32, (iv) a radioactive metal such as chromium 51, calcium 45, cobalt 57, iron 59, (v) a toxic material such as ethidiun bromide, (vi) a chelator such as CDTA (trans-1,2-Diaminocyclohexane-N,N,N',N'-tetraacetic acid), EDTA (Ethylenediamine tetraacetic acid), EGTA (Ethylenenglycol-O,O'-bis(2-aminoethyl)-N,N,N',N'-tetraacetic acid), DTPA (Diethylenetriamine pentaacetic acid), HEDTA (N-(2-Hydroxyethyl)ethylenediamine-N,N,N'-triacetic acid), NTA (Nitrilotriacetic acid), TTHA (Triethylenetetramine-N,N,N',N",N'",N'"-hexaacetic acid), Dimethyl-BAPTA (Molecular Probes, USA), citric acid or BAPTA (Bis (2-aminophenoxy)ethane-N,N,N',N'-tetraacetic acid). The chelator is usually found in the form of a salt with one or more of the following; sodium, potassium, lithium, calcium, copper, ammonium, zinc, iron, magnesium, manganese, tetramethylammonium, tetraethylammonium or tetrabutylammonium. The undesired chelator is capable of binding by chelation to a metal located on the solid phase such as calcium on hydroxylapatite solid phase. Preferably, the undesired constituent bears either a net positive or negative charge or has a sufficiently polarised charge distribution so that it can be bound to the solid phase via a charge attraction. More preferably, the undesired constituent bears a negative charge so that it can be bound and removed using surface coated hydroxylapatite.

Where the undesired constituent is a nucleotide, a chelator, an anionic detergent or a negatively charged amino acid such as glutamic acid or aspartic acid, and the desired analyte to be purified is a nucleic acid or a protein, then preferably the solid phase is hydroxylapatite and the surface coating is a nucleic acid.

Where the undesired constituent is a positively charged amino acid such as lysine or arginine acid, and the desired analyte to be purified is a positively charged protein, then preferably the solid phase is hydroxylapatite and the surface coating is a positively charged polymer such as nylon or polyglutamic acid.

As mentioned above, the solid phase could be one with a net negative or positive charge, be hydrophobic, have affinity for a molecule for example via an antigen-antibody complex or have size exclusion properties. Examples of suitable solid phases include agarose, acrylamide, polyethylene, polycarbonate, polypropylene, polystyrene, acrylic, quartz, rubber, polyester, polyvinyl chloride, polyurethane, nylon, glass, hydroxylapatite, fluorapatite, silica, a metal, a metal salt or a metal oxide. The metal or the metal present in the metal salt or metal oxide may be calcium, iron, chromium, gallium, germanium, lithium, magnesium, manganese, pallidium, cesium, tungsten, selenium, tin, vanadium, molybdenum, nickel, copper, zinc, aluminium, silver, gold, platinum or lead. The solid phase may also comprise a mixture of metals such as an iron-zinc blend or an oxide thereof, for example lithium iron III oxide.

Preferably the solid phase contains a magnetic component such as iron, allowing simplified mixing and separation of the particle from the analyte containing mixture. Magnetic hydroxylapatite, which is particularly suited to practising this invention, is commercially available (Hydroxylapatite Type I, Chemicell Gmbh, Germany).

The physical process by which the contaminant is bound to the solid phase can be one or more of the following; adsorption, absorption, charge, hydrophobicity, affinity, hydrogen bonding or covalent. The binding interaction between the contaminant and the surface treated solid phase need not be permanent and an equilibrium may exist between bound and non-bound contaminant, the interaction should be sufficiently permanent to allow the removal of the contaminant at the same time as the surface treated solid phase.

The solid phase could be in the form of a bead, a particle, a magnetic bead or particle, a sheet, a gel, a powder, a filter, a membrane, or be attached to the interior of a tube or as the packing of a chromatography column, or on the lining of a well such as 96, 384 or 1536 formats, or a pipette tip or on a surface of an elongated probe capable of entering into a vessel. In each case, the solid phase is coated with a surface treatment that provides a means to differentially separate the analyte from the undesired constituent. It could also be a membrane containing pores of a defined size so that the entry of an analyte molecule into the pore is controlled not only by the size of the pore itself but also the charge surrounding and within the pore itself.

Following removal of the contaminant from the analyte, the surface treated solid phase can be removed from the analyte containing solution using any one of a number of methods such as; (i) collection of magnetic particles with a magnet, (ii) collecting the solid phase with a filter such as a 0.05, 0.1 or 0.2 µm Millipore polycarbonate filter, or (iii) separation by centrifugation or sedimentation.

The invention therefore relates to the combination of one or more solid phases which may be a material such as hydroxylapatite with one or more specialised surface treatments thereby restricting the interaction of molecules within the sample with the material.

The attachment of the surface treatment to the material is not particularly limited but can be covalent, ionic, encapsulation coating, adsorption, absorption or a hydrophobic interaction. The surface treatment must be sufficiently dense to at least cover, in its entirety the underlying surface phase at a density such that there is useful separation of the undesired component from the analyte. The density and suitability of the surface treatment can be empirically determined by adding progressively less of the surface treatment to a fixed amount of solid phase until the desired separation property of a labelled analyte from the undesired component is lost. This can be readily determined by using for example a radioactive or fluorescently labelled analyte and/or undesired constituent. It is preferred that more than 50% of the undesired reaction component is removed from the analyte, more preferably at least 75%, even more preferably at least 90% and most preferably 100%. It is also preferred that less than 50% of the desired analyte is lost during the separation of the undesired constituent, more preferably less than 25%, even more preferably less than 10% and most preferably 0%.

It is preferable that the surface treatment material is sufficiently firmly attached to the underlying solid phase that it does not fall off, leech or in any other way contaminate the analyte containing mixture. The attachment strength can be determined by incubating the surface treated solid phase in the same solvent as the analyte and measuring the loss of the surface treatment from the solid phase by for example weighing, IR spectrophotometry or u/v absorption or loss of the desired separation property from the solid phase. Alternatively, the surface treatment can be labelled with for example fluorescence and the rate of appearance of fluorescence in the analyte containing solvent measured. If the surface treatment is a polynucleotide, it is preferred that it is a non-coding homopolymer chosen from, for example, poly r(C), poly r(U), poly r(G), poly r(A), or poly d(C), poly d(T), poly d(U), poly d(G), poly d(A), or poly d(A/T), poly d(U/A) or poly d(G/C) so that it is less likely to interfere with sensitive downstream applications such as reverse transcription or protein translation. Ribopolynucleotides such as poly r(C) or poly r(A) surface coating can be stabilised from attack by ribonucleases and hydrolysis by modification of the 2'-OH groups with for example acetyl as set out in patent applications WO/01/94626 and WO/00/75302. Ribopolynucleotides can also be covalently cross-linked using glutaldehyde or sebacoyl chloride as set out in patent applications WO/01/94626 and WO/00/75302. The covalent cross-linking produces an interlocked mesh on the exterior of the solid phase so that any one molecule of a polyribonucleotide is less likely escape from the surface of the solid phase. DNA strands can also be cross-linked by for example adriamycin treatment (Cullinane et al, (2000) Nucleic. Acids. Res. 28:1019), mitomycin C, glutaldehyde or u/v cross linking. The cross linking of DNA and RNA is well known in the art and the particular method is not limited, however sufficient cross linking should be obtained to reduce leeching of the surface treatment to a level where it does not interfere with the downstream application and analysis of the analyte.

Polyribonucleotides are sometimes added as enhancers of reverse transcription (HCV Amplicor v2.0, Roche, USA) so the leaching of the surface treatment into the analyte is not necessarily undesired. However, when the downstream use of the analyte is not particularly sensitive to contamination with the surface treatment, for example, the removal of labelled nucleotides from radioactive probes for Southern blotting, then the type of polynucleotide is not particularly important so that coding polynucleotiodes, for example genomic DNA such as single or double stranded salmon sperm DNA can be used. Such sources of polynucleotides for surface treatment can be more economical than homopolymers that are produced by an in vitro enzymatic or synthetic reaction.

When the surface treatment is a polynucleotide, it is not especially limited by the sequence, save for the reasons expressed above. It can be a single, double or triple stranded homopolymer, a single, double or triple stranded hetero oligo- or polynucleotide such as prokaryotic or eukaryotic genomic DNA such as *E. coli*, plant or salmon or herring sperm genomic DNA, a phage such as Lambda phage, M13, or virus such as BMV or TMV derived nucleic acid, mitochondrial DNA, total RNA, rRNA, tRNA or mRNA. The nucleic acid can be synthesized from an in vivo or in vitro source such as during an RNA polymerase reaction or PCR or during in vitro DNA synthesis. The length of the oligo- or polynucleotide is not particularly limited, however, longer sequences are preferred when used in combination with hydroxylapatite solid phases so that there is an increased chance that there are at least two or more points of charge interaction between the nucleic acid surface treatment and the hydroxylapatite, thereby reducing the amount of the surface treatment that may become unbound from the hydroxylapatite and contaminate the analyte containing solution. Typically, sequences of at least 20 nucleotides in length are used. Preferably, the sequences are at least 50 nucleotides, more preferably 250 nucleotides, even more preferably 500 nucleotides and most preferably over 2000 nucleotides in length. The nucleic acid can be either single, double or triple stranded, however, double stranded is preferred because it is an economical source and has a higher affinity for hydroxylapatite than single stranded nucleic acids because of its increased charge. The nucleic acid need not be salt free, for example lithium, potassium, sodium, manganese or magnesium salts of the nucleic acid phosphate groups can be employed as the surface coating. Salt free nucleic acid surface coatings have a higher negative charge and therefore have a stronger interaction with hydroxylapatite so that less of the surface coating is lost into the analyte containing sample. However, following tests, such salt free coatings did not have noticeably improved separation qualities compared with salts of the same nucleic acid coatings.

Homopolymers of RNA and DNA, which are particularly preferred for surface treatment of hydroxylapatite, are commercially available as either single or double stranded molecules (Midland Certified Reagent Company, USA and Amersham Biosciences, UK).

The surface coating can also be composed of non-biological materials providing that it can provide a sufficient coating over the entire solid phase in the form of a mesh so that small non-desired molecules can traverse the mesh and become immobilised on the solid phase, whilst larger molecules are blocked from doing so. Such materials can include nylon fibres, polyamides, polycations, polyanions and polyvinylamine. Non-charged surface coatings may also be used to impede the contact of larger analyte molecules such as DNA from contacting the solid phase such as hydroxylapatite. For neutral polymer coatings, such as polyethylene oxide and polypropylene oxide, acrylamide and agarose their interaction with the underlying hydroxylapatite is not by charge and therefore the hydroxylapatite has to be encapsulated by a thin film of the neutral coating so the coating is not detached and lost during use. The coating in this case should be sufficiently thin to allow rapid diffusion of the undesired constituent but sufficiently thick to impede contact between the analyte and the solid phase. Such measurements can be defined empirically using a labelled analyte and undesired constituents.

The analyte containing mixture can be presented to the separation material either in a liquid such as water, a buffer, a chelator such as EDTA or EGTA, an enzymatic reaction, a cellular or biological fluid such as a cell lysate, serum or cell supernatant used for drug discovery, a homogenised clinical sample, or an organic solvent such as ethanol, DMSO, toluene, tetrahydrofuran or acetonitrile. Alternatively, the mixture containing the analyte and undesired constituent can be in the gas phase or a vapour so that for example a gaseous mixture is pumped through or over the separation mixture consisting of the surface treated solid phase and the purified exhaust gases captured for analysis.

The invention could also be used in combination with another separation process such as filtration, gas chromatography, dialysis or affinity chromatography to render the removal of the undesired constituent in a more precise manner. Indeed the invention is not especially limited as to the type of downstream application that the purified analyte is used for. Such applications include but are not limited to: Southern and Northern blotting; gel electrophoresis of nucleic acids and proteins; electroblotting; cDNA synthesis; PCR amplification; one-step and two-step RT-PCR amplification; ligase chain reaction (LCR) amplification; transcription mediated amplification (TMA); single nucleotide polymorphism analysis (SNP); various forms of chromatography such affinity, ion exchange, hydrophobic interaction, reversed phase and gel filtration; various forms of mass spectrometry (MS) such as, gas chromatography-MS, SELDI, MALDI-TOF, ESI, MS/MS or FT-ICR; capillary electrophoresis particularly of fluorescent dye labelled sequencing reactions and SNP assays using commercial systems such as the ABI Prism 3100, or ABI 3730 (Applied Biosystems, USA) where the removal of unincorporated fluorescent sequencing nucleotides is critical. Indeed, this invention can also be used to remove dNTP's following PCR amplification but preceding the sequencing reaction itself. In this case, it is critical that all the unlabelled nucleotides that were not incorporated into the PCR product during amplification are removed otherwise they will interfere with the sequencing reaction. Currently, unincorporated nucleotide triphosphates are removed following PCR using shrimp alkaline phosphatase (see ExoSAP-IT (Amersham Biosciences; catalogue number US78200). By treating the PCR reaction, post-amplification with the surface treated solid phase as set out in this invention effectively removes the free nucleotides from the PCR product leading to a successful sequencing reaction. This is particularly well suited to high throughput sequencing and SNP applications.

The invention provides a simple means to remove a labelled molecule from a sample, thereby allowing the quantitation and analysis of the amount of the label that has been metabolized by for example cellular enzymes, or incorporated into a polymer, or broken down (catabolized). This is particularly useful for drug discovery applications for example employing assays to determine the incorporation of 3H labelled thymidine.

Whilst nucleic acid attachment to a solid phase for purification purposes (for example Immobilised DNA, catalogue number 27-5575-02, and Polynucleotide affinity, catalogue number 17-0860-01, Amersham Biosciences, UK), the purpose of these products is to capture biomolecules such as proteins and RNA on the surface of the solid phase by way of an affinity interaction (Greth et al., (1975) Biochem. Biophys. Acta. 390:168). In contrast, the nature of the present invention is not to bind molecules on its surface, rather it is to selectively stop a proportion of the desired analyte molecules from binding to the solid phase whilst allowing the non-desired contaminant molecules to be bound to the solid phase and therefore removed. Therefore the primary action of the surface treatment is to form a selective barrier to the underlying solid phase.

In certain cases it is desirable to remove two or more contaminants from the solution containing the desired analyte. Removal of multiple contaminants can be achieved either by (i) all the contaminants binding to the underlying solid phase, such as in the example when each contaminant has the same net charge, (ii) the solid phase has a mixture of binding properties such as chelator binding activity and charge, (iii) there are separate solid phases, each with a distinct binding property which are either (a) in direct physical contact with one another as in an agglomerate or (b) in two or more separate particles but used together at the same time or successively, or (c) found in independent but overlapping layers such as in multiple shells surrounding a central magnetic particle, and (iv) where one or more of the contaminants is removed by a combination of binding to the solid phase and by binding to the surface.

When the surface treatment is an oligo- or polynucleotide, the surface treatment can provide two different functions; firstly, as set out above, as a selective barrier to the analyte and secondly, as an affinity capture reagent specific for particular nucleotide sequences. For example, if the oligo- or polynucleotide sequence is complementary to a specific sequence such as a human repetitive DNA element then it would be a means to remove not only smaller molecules by means of acting as a selective barrier but also by capturing a sub-group of nucleotide sequences in the analyte mixture. In this way, non-desired nucleic acid sequences can be removed simultaneously with the non-desired molecules such as EGTA or other chelators, or free nucleotides leaving the purified desired analyte in solution ready to be analysed. For example, when an oligonucleotide or peptide nucleic acid complementary to a human repetitive sequence such as a Line-1 element is bound on the exterior of magnetic hydroxylapatite beads (Chemicell, Germany) then the surface treated solid phase beads are efficient at removing both the dNTP's and the contaminating human genomic sequences post-PCR.

The method as described in the invention can involve either a single or multiple steps. For example the surface treated solid phase can be applied once to the solution containing the contaminant and analyte to remove 90% of the contaminant, then the analyte containing solution is treated a second or several more times with fresh surface treated solid phase to remove progressively the remaining 10% of the contaminant. Alternatively, different types of surface treated solid phases can be added to the analyte containing solution in series or at the same time in order to remove contaminants with two or more different properties such as charge and hydrophobicity. There are no particular restrictions about the order of addition of the materials or solutions. For example the surface treated solid phase can be added to the analyte containing solution or vice versa. It may also be preferable to treat the solution containing the contaminant with a fraction (10%) of the total of the surface treated solid phase, allow binding to occur, remove the solid phase and then treat the solution a second or more times with the remaining 90% of the surface treated solid phase either progressively, for example with nine portions of 10% or in a single batch of 90%. Adding the surface treated solid phase in portions may improve the amount of contaminant(s) removed and reduce the amount of analyte lost. The preferred treatment method can be determined empirically using for example a radioactively tagged contaminant and/or analyte.

It may also be desirable in certain cases to capture the 'contaminant' rather than the analyte. For example, many modified nucleotides are expensive and only a small proportion are incorporated into a polynucleotide during polymerisation. Following polymerisation, the valuable nucleotides can be captured with the surface coated solid phase as prepared in Example 1, and later released by elution from the solid phase using a sodium phosphate or chelator such as EGTA to remove the dNTP when the solid phase is hydroxylapatite.

The surface coated solid phase may also serve as part of an assay, for example, following a DNA 32P dCTP labelling reaction, and capture with a solid phase as prepared in Example 1, the amount of radioactivity associated with the solid phase is a direct measure of the efficiency of the incorporation of 32P into the DNA. Scintillation counting of the surface coated solid phase therefore serves as part of an assay, for example a single nucleotide polymorphism assay. Other assays could include a measure of the amount of a fluorescently labelled amino acid or nucleotide bound to the surface treated solid phase compared with the non bound labelled polymer. Therefore in certain instances the material that can bind to the surface coated solid phase itself serves as the analyte for the assay. Measurements of fluorescence or radioactivity or other labels are straightforward using a scintillation counter of fluorimeter and are well known by those skilled in the art.

Preferred Method of Use

Hydroxylapatite, also known as hydroxyapatite is a naturally occurring mineral primarily composed of calcium phosphate. It is widely used in the manufacture of a variety of bioimplants and chromatography materials. Chromatography using hydroxylapatite is a well-established method and is principally used for the separation and purification of proteins, DNA and RNA (Sambrook et al., (1989) Molecular Cloning: A Laboratory Manual, CSH).

The interaction is based either on the ionic attraction between a positive charge on the sample molecule and the negative phosphate charge of the hydroxylapatite or a negative charge on the sample molecule and the positive charge of the calcium.

For the hypothetical example of two molecules of identical molecular weight and size but one molecule has no charge and the other a charge of −1. If the surface coating of the membrane is negative, then the uncharged molecule will preferentially pass through the pores of the membrane, whilst the negatively charged molecule will be repulsed and therefore be less likely to enter the pore. The uncharged molecule could be induced to pass through the pore by diffusion, capillarity, pressure or centrifugal force. The uncharged molecule could be detected by a variety of methods including a scintillation proximity assay, a fluorescence assay or colorimetric detection. In the case of two molecules with the same charge but of varying molecular weight, the smaller molecular will tend to pass more readily through the surface coating and contact the solid phase compared than the larger molecule.

The invention will now be further described with the aid of the following examples. The experimental details are not intended to be limiting.

EXAMPLE 1

Preparation of a Surface Coated Solid Phase

Preparation of nucleic acid surfaces on magnetic hydroxylapatite: To 10 µl (50 mg/ml) of magnetic hydroxylapatite Type-I (Chemicell, Germany) in a 1.5 ml polypropylene microcentrifuge tube was added 25 µl of water containing 25 µg of the homopolymer poly d(A) (Midland Certified Reagent Company, USA) and mixed for 10 minutes at 25° C. using the 0.5 sec. step program of a MCB1200 magnetic mixer (Dexter Magnetics, UK). The beads were collected with the MCB1200 magnet, the liquid removed from the Type-I beads and the beads washed three times with 0.5 ml water each, before finally being resuspended in a final volume of 10 µl water. Alternatively, poly d(A) can be replaced with the same amount of poly d(T), poly d(U), poly d(C), poly d(G), poly d(I), poly r(A), poly r(U), poly r(C), poly r(G), poly d(A/T), poly d(C/G), poly d(I/C), poly r(A/U), poly r(A)d(T), poly r(U)d(A), poly r(C)d(G), poly r(G)d(C), BMV RNA (Promega, USA), ssM13 DNA (Amersham Biotech, UK), pUC plasmid DNA, human genomic DNA, single or double stranded salmon or herring sperm DNA (Sigma-Aldrich, USA), 25-50-mer oligonucleotides (MWG, Germany. There is no particular limitation to the type of nucleic acid used except that small amounts of heteropolymers that leach from the magnetic hydroxylapatite such as poly d(I/C) have been found to lead to non-specific PCR amplification products when used to purify templates for PCR amplification. Therefore, for this purpose, non-coding single stranded homopolymers such as poly r(A) are preferred.

EXAMPLE 2

Removing 32P Alpha-labelled Deoxynucleotide Triphosphates from Solution

A comparison was made of four types of nucleic acid coated hydroxylapatite beads prepared as in Example 1 in order to determine whether a particular type of nucleic acid provided improved separation properties.

Preparation of nucleic acid surfaces on magnetic hydroxylapatite: To 10 µl (50 mg/ml) of magnetic hydroxylapatite Type-I (Chemicell, Germany) in a 1.5 ml polypropylene microcentrifuge tube was added 25 µl of water containing 25 µg of either the homopolymer poly d(I/C), poly r(A), poly r(C) or poly d(A) (Midland Certified Reagent Company, USA) and mixed for 10 minutes at 25° C. using the 0.5 sec. step program of a MCB1200 magnetic mixer. The beads were collected with the MCB1200 magnet, the liquid removed from the Type-I beads and the beads washed three times with 0.5 ml water each, before finally being resuspended in a final volume of 10 µl water. The beads were then tested in two separate experiments, for their capacity to bind either free 32P dATP nucleotides or a 32P labelled mixture of a purified 250 and 1700 nt in vitro transcribed RNA. To 5 µl of the nucleic acid-bead mixture was added either 50 µl of water containing $5 \times 10^3$ cpm 32P dATP or $5 \times 10^3$ cpm of RNA. The magnetic beads and radioactive test compound were mixed for 5 minutes at 25° C. using a MCB1200 magnetic mixer, before the beads were collected on the side of the tube using a magnet, the liquid removed and both the radioactivity associated with the beads or liquid quantitated by scintillation counting. The results are shown in Table 1, whilst all nucleic acid-hydroxylapatite beads were capable of removing at least 94% of the free nucleotides, poly r(A) was the most effective at preventing the binding and therefore the loss of the RNA analyte.

TABLE 1

| Nucleic acid surface treatment type | % 32P nucleotides removed from solution | % 32P RNA polynucleotide removed from solution |
|---|---|---|
| Poly d(I/C) | 94 | 19 |
| Poly r(C) | 97 | 14 |
| Poly r(A) | 95 | 10 |
| Poly d(A) | 95 | 16 |

EXAMPLE 3

Determining the Minimal Amount of Nucleic Acid Required to Coat a Specified Amount of Magnetic Hydroxylapatite Different amounts of poly d(A) were mixed separately with 10 µl (50 mg/ml) of magnetic hydroxylapatite Type-I (Chemicell, Germany) and then tested for the capacity of the nucleic acid-bead mixture to bind a 32P labelled purified mixture of a 250 and 1700 nt in vitro transcribed RNA in order to determine the minimum required amount.

Preparation of nucleic acid surfaces on magnetic hydroxylapatite: To 10 µl (50 mg/ml) of magnetic hydroxylapatite Type-I (Chemicell, Germany) in a 1.5 ml polypropylene microcentrifuge tube was added 25 µl of water containing either 250, 125, 75 ng or no poly d(A) (Midland Certified Reagent Company, USA) and mixed for 10 minutes at 25° C. using the 0.5 sec. step program of a MCB1200 magnetic mixer (Dexter Magnetics, UK). The beads were collected with the MCB1200 magnet, the liquid removed from the Type-I beads and the beads washed three times with 0.5 ml water each, before finally being resuspended in a final volume of 10 µl water. The results are shown in Table 2.

TABLE 2

| Amount of poly d(A) | % 32P RNA polynucleotide removed from solution |
|---|---|
| 250 ng | 9.3 |
| 125 ng | 7.1 |
| 75 ng | 30 |
| 0 ng | 50 |

It was found that between 75-125 ng of poly d(A) was required per 10 µl magnetic hydroxylapatite Type-I (Chemicell, Germany).

EXAMPLE 4

Removing Unincorporated 32P Alpha-labelled Deoxynucleotide Triphosphates from a Labelled DNA Polymer A DNA labelling reaction was carried out according to Basic Protocol 3 (Short Protocols in Molecular Biology, 4$^{th}$ Edition, Editor Ausubel et al., 1999, Wiley Publishers, pg 3-20 to 3-21), except that at step 6, the unincorporated radioactive precursors were removed as follows, 10 µL of hydroxylapatite-nucleic acid beads prepared as in Example 1 were added following completion of the reaction and mixed for 5 minutes at 25° C. using a MCB1200 magnetic mixer, before the beads were collected on the side of the tube using a magnet and the remaining liquid containing the 32P labelled analyte DNA probe removed for hybridisation purposes using standard conditions. As an alternative to the use of the MCB1200, the bead and reaction can simply be incubated together without agitation for 15 minutes at room temperature, before separation of the beads with a magnet or centrifugation and recuperation of the analyte containing liquid.

EXAMPLE 5

Removing Unincorporated 32P Gamma-labelled Deoxynucleotide Triphosphates from a Labelled DNA Oligonucleotide An oligonucleotide labelling reaction was carried out according to Support Protocol (Short Protocols in Molecular Biology, 4$^{th}$ Edition, Editor Ausubel et al., 1999, Wiley Publishers, pg 6-10). Following the labelling reaction, the unincorporated radioactive gamma labelled precursor nucleotides were removed as follows; 10 μl of hydroxylapatite-nucleic acid beads prepared as in Example 1 were added to the reaction and mixed for 5 minutes at 25° C. using a MCB1200 magnetic mixer, before the beads were collected on the side of the tube using a magnet and the remaining liquid containing the 32P labelled analyte DNA probe removed for hybridisation purposes using standard conditions. As an alternative to the use of the MCB1200, the bead and reaction can simply be incubated together without agitation for 15 minutes at room temperature, before separation of the beads with a magnet or centrifugation and recuperation of the analyte containing liquid.

EXAMPLE 6

Removing Unincorporated dNTP's from a PCR Reaction

A PCR is carried out in a final volume of 25 μl with final concentration of 15 mM Tris-HCl pH 8.8, 60 mM KCl, 2.5 mM $MgCl_2$, 400 μM each dNTP, 10 pmol of each primer SP6 and T3 and 0.25 unit Taq DNA polymerase (Amersham, UK). Cycle parameters were 94° C.×20 sec, 55° C.×20 sec and 72° C.×30 sec for 30 cycles. Following the PCR, free unincorporated dNTP's and inorganic pyrophosphate (PPi) was removed by adding 10 μl of hydroxylapatite-nucleic acid beads prepared as in Example 1 were added to the reaction and mixed for 5 minutes at 25° C. using a MCB1200 magnetic mixer, before the beads were collected on the side of the tube using a magnet and the remaining liquid containing the 32P labelled analyte DNA probe removed for hybridisation purposes using standard conditions. As an alternative to the use of the MCB1200, the bead and reaction can simply be incubated together without agitation for 15 minutes at room temperature, before separation of the beads with a magnet or centrifugation and recuperation of the analyte containing liquid.

The PCR components are not limited to any one type, indeed nucleotides can be removed from a number of different types of reactions such as those employing Tth DNA polymerase, bicine buffers and Manganese divalent metal ions. PCR products purified in this manner can be used directly for further applications such as cycle DNA sequencing where unincorporated nucleotides carried over from the PCR strongly inhibit the sequencing reaction. In the case of PCR reactions where high concentrations of dNTP's are used, a second lot of the surface treated solid phase may need to be added.

EXAMPLE 7

Removing Excess Salt Ions from a Sample Prior to Mass Spectrometry Analysis

Electrospray, SELDI and MALDI mass spectrometry are strongly influenced by residual salts carried over with the analyte molecules such as proteins and nucleic acids. Beads as prepared in Example 1 can be used to remove such contaminating ions prior to analysis as follows; 2 μl of hydroxylapatite-nucleic acid beads prepared as in Example 1 were added to the salt containing analyte sample and mixed for 5 minutes at 25° C. using a MCB1200 magnetic mixer, before the beads were collected on the side of the tube using a magnet and the remaining liquid containing the salt free analyte molecule treated as usual before analysis before mass spectrometry. As an alternative to the use of the MCB1200, the bead and sample can simply be incubated together without agitation for 15 minutes at room temperature, before separation of the beads with a magnet or centrifugation, recuperation and analysis of the analyte containing liquid.

EXAMPLE 8

Removing Unincorporated 32P Labelled Ribonucleotide Triphosphates from a Labelled RNA Polymer An in vitro transcription reaction using T7 RNA polymerase Riboprobe® Kit and pGEM express positive control template (Part No.s P1440 and P256A, Promega, USA) was prepared according to the manufacturer's instructions with the inclusion of 5 μl of 32P rUTP. Template DNA was removed by the addition of 1 unit of RNase free DNase RQ1 and incubating for 15 min at 37° C. The 32P labelled RNA transcripts generated in the reaction were contaminated with significant amounts of residual unincorporated 32P rUTP which was removed as follows; 10 μl of hydroxylapatite-nucleic acid beads prepared as in Example 1 were added to the reaction and mixed for 5 minutes at 25° C. using a MCB1200 magnetic mixer, before the beads were collected on the side of the tube using a magnet and the remaining liquid containing the 32P labelled analyte RNA probe removed with a pipette tip. As an alternative to the use of the MCB1200, the bead and reaction can simply be incubated together without agitation for 15 minutes at room temperature, before separation of the beads with a magnet or centrifugation and recuperation of the analyte containing liquid.

EXAMPLE 9

Removing Unincorporated Labelled Amino Acids from a Labelled Protein

A fluorescently labelled in vitro translated luciferase protein was generated using a FluoroTect™ GreenLys and TnT T7 Coupled Reticulocyte lysate Kit (Part No. L5001 and L4610, Promega, USA) or a Transcend™ Biotinylated Lys Kit (Part No. L5001, Promega, USA) and a luciferase mRNA template using manufacturer's instructions. Following the reaction step, the tRNA-labelled Lys molecule was degraded by incubating for 10 minutes at 37° C. with 1 μl of RNase One™ (Part No. M4261, Promega, USA). This step is important to reduce the molecular weight of the labelled Lys by degrading the tRNA, thereby allowing the small labelled Lys molecule to traverse the coating and bind to the solid phase.

The coated solid phase was prepared as follows. To 10 µl (50 mg/ml) of magnetic hydroxylapatite Type-I (Chemicell, Germany) in a 1.5 ml polypropylene microcentrifuge tube was added 25 µl of water containing 25 µg of poly-lysine (Sigma-Aldrich, USA) and mixed for 10 minutes at 25° C. using the 0.5 sec. step program of a MCB1200 magnetic mixer (Dexter Magnetics, UK). The beads were collected with the MCB1200 magnet, the liquid removed from the Type-I beads and the beads washed three times with 0.5 ml water each, before finally being resuspended in a final volume of 10 µl water. Alternatively, poly-arginine or poly-histidine (Sigma-Aldrich, USA) may also be used as coatings. There is no particular limitation to the type of polycation used for the coating except that the overall net charge should be positive if the protein to be purified has a net positive charge and the contaminating labelled amino acid has an overall positive charge. Negatively charged proteins can be separated from contaminating negatively charged labelled amino acids such as aspartic acid and glutamic acid by substituting the 25 µg of poly-lysine with 25 µg of poly-aspartic acid or poly-glutamic acid (CarboMer, USA) as the coating. For all preparations, 10 µl of the coated hydroxylapatite was mixed with 20 µl of the protein translation mixture and mixed for 10 minutes at 4° C. using the 0.5 sec. step program of a MCB1200 magnetic mixer (Dexter Magnetics, UK). The beads were collected with the MCB1200 magnet, and the liquid containing the purified protein removed and analysed. For certain proteins with a weak positive, neutral or weak negative charge, it is possible to use either a positively or negatively charged or neutral surface treatment of the solid phase. Preferably the solid phase is hydroxylapatite. If the desired analyte is partially retained by interactions with the surface treatment it can be removed by washing the material with weak concentrations of detergents such as SDS or Triton.

EXAMPLE 10

Removing Sodium Dodecyl Sulphate (SDS) from a Solution

Sodium dodecyl sulphate (SDS) and sodium lauryl sulphate (SLS) are negatively charged (anionic) detergents that although are frequently used for protein applications can lead to serious impairment of various downstream applications of proteins such as enzyme and antibody assays because the detergent disrupt protein structures. It is tedious and labour intensive to remove such detergents from proteins by dialysis or filtration. An improved method uses nucleic acid coated hydroxylapatite prepared as in example 1 and used as follows; Up to 1% of a SDS, SLS or other anionic detergent contaminated protein solution in 20 µl volume of 10 mM Tris HCl buffer, 1% BSA was added to 10 µl of coated solid phase prepared according to Example 1, and mixed for 10 minutes at 4° C. using the 2 sec. step program of a MCB1200 magnetic mixer (Dexter Magnetics, UK). The beads were collected with the MCB1200 magnet, the liquid containing the detergent free protein removed and the beads discarded.

EXAMPLE 11

Removing EGTA from a Nucleic Acid Solution

Preparation of nucleic acid surfaces on magnetic hydroxylapatite: To 10 µl (50 mg/ml) of magnetic hydroxylapatite Type-I (Chemicell, Germany) in a 1.5 ml polypropylene microcentrifuge tube was added 25 µl of water containing 25 µg of the homopolymer poly r(A) (Midland Certified Reagent Company, USA) and mixed for 10 minutes at 25° C. using the 0.5 sec. step program of a MCB1200 magnetic mixer (Dexter Magnetics, UK). The beads were collected with the MCB1200 magnet, the liquid removed and the beads washed three times with 0.5 ml water each, before finally being resuspended in a final volume of 10 µl water. Alternatively, poly r(A) can be replaced with the same amount of poly d(T), poly d(U), poly d(C), poly d(G), poly d(I), poly r(U), poly r(C), poly r(G), poly d(A/T), poly d(C/G), poly d(I/C), poly r(A/U), poly r(A)d(T), poly r(U)d(A), poly r(C)d(G), poly r(G)d(C), 25-50-mer oligonucleotides (MWG, Germany). There is no particular limitation to the type of nucleic acid used except that small amounts of heteropolymers that leach from the magnetic hydroxylapatite such as poly d(I/C) have been found to lead to non-specific PCR amplification products when used to purify templates for PCR amplification. Therefore, for this purpose, non-coding single stranded homopolymers such as poly r(A) are preferred.

Such beads are useful to remove chelators from RNA solutions that have been eluted from magnetic hydroxylapatite as set out in the examples of the patent application GB 0217963.8 (priority date $2^{nd}$ Aug. 2003). In these examples, magnetic hydroxylapatite is used to capture either RNA such as HIV, West Nile Virus or HCV derived from blood or plasma, however, unlike silica, the nucleic acids cannot be eluted using only water and a chelator such as EGTA has been found by the applicant to be effective means to remove the nucleic acid from the magnetic hydroxylapatite. However, for certain downstream applications, in particular RT-PCR using the enzyme Tth DNA polymerase, it has been found that the activity of the enzyme is reduced in the presence of excess chelator. This is because the manganese ions in the reaction that are essential for Tth activity are sequestered by the chelator and this reduces the enzyme activity. It is therefore essential to remove a large proportion of the chelator from the nucleic acid solution if the RNA is to be efficiently copied and amplified using Tth DNA polymerase found for example in the diagnostic kits Ampliscreen and Amplicor HIV and HCV (Roche Diagnostics, USA). Whilst several means to remove the chelator from the nucleic acid. solution have been set out by the current applicant in application GB 0217963.8, it has been found that the most effective means is to use nucleic acid coated magnetic hydroxylapatite, and prepared as set out in this example.

The volume of the elution solution containing the chelator is variable and can be within the range of 25-400 µl. The preferred elution solution as set out in GB 0217963.8 is 10 mM EGTA, pH 10.2. Following elution, the residual EGTA concentration is usually reduced to approximately 3-5 mM, however there is no particular limitation to the amount of EGTA or other chelator that can be removed from solution; for larger amounts of chelator a correspondingly larger amount of the nucleic acid coated magnetic hydroxylapatite can be used.

Following elution as set out in the examples of GB 0217963.8; to 200 µl of the chelator/nucleic solution (approximate final residual EGTA concentration 5 mM EGTA) is added 20 µl of the nucleic acid coated magnetic hydroxylapatite prepared as set out in this example using poly r(C) to coat the beads. The nucleic acid coated magnetic hydroxylapatite beads are mixed with the chelator/nucleic solution for 10 minutes at 25° C. using the 0.5 sec. step program of a MCB1200 magnetic mixer (Dexter Magnetics, UK) during which period, the chelator is bound to the hydroxylapatite underlying the poly r(C) coating but the desired analyte nucleic acid does not bind to the hydroxylapatite because of the poly r(C) coating. The beads are then collected with the MCB1200 magnet and the liquid containing the chelator free nucleic acid, removed from the nucleic acid coated magnetic hydroxylapatite beads and used directly in the assay, containing for example, Tth DNA polymerase. For larger volumes or higher residual concentrations chelator in the elution solution, a correspondingly larger amount of the nucleic acid coated magnetic hydroxylapatite can be used.

The chelator can be any one of several that has affinity for hydroxylapatite, for example; CDTA (trans-1,2-Diaminocyclohexane-N,N,N',N'-tetraacetic acid), EDTA (Ethylenediamine tetraacetic acid), EGTA (Ethylenenglycol-O,O'-bis(2-aminoethyl)-N,N,N',N'-tetraacetic acid), DTPA (Diethylenetriamine pentaacetic acid), HEDTA (N-(2-Hydroxyethyl)ethylenediamine-N,N,N'-triacetic acid), NTA (Nitrilotriacetic acid), TTHA (Triethylenetetramine-N,N,N', N'',N''',N''''-hexaacetic acid), Dimethyl-BAPTA (Molecular Probes, USA) or BAPTA (Bis(2-aminophenoxy)ethane-N,N, N',N'-tetraacetic acid).

The desired nucleic acid in the elution can be RNA, DNA, a hybrid of RNA and DNA, single or double stranded, linear or circular and be derived from a plant, an animal, a bacteria, a virus, a diagnostic sample such as blood or body fluid. The desired nucleic acid can be viral RNA, tRNA, rRNA, mRNA, hnRNA, an aptamer, a plasmid, an oligonucleotide, a polynucleotide, genomic DNA, viral DNA or a ribozyme.

EXAMPLE 12

Removing Sodium Phosphate from a Polymer Eluted from HPA

Sodium phosphate solutions are commonly used to elute nucleic acids from hydroxylapatite (Sambrook et al., (1989) Molecular Cloning: A Laboratory Manual, CSH; Jones (1995) Gel Electrophoresis: Nucleic Acids Essential Techniques, Wiley) but are difficult to separate from the nucleic acid except by dialysis or filtration as, unfortunately, nucleic acids cannot be precipitated from sodium phosphate solutions. Excess amounts (10-50 mM) of sodium phosphate (pH 5-7) contaminants can be removed from nucleic acids as follows; 10 µl of hydroxylapatite-nucleic acid beads prepared as in Example 1 were added to the sodium phosphate/nucleic acid mixture and mixed for 5 minutes at 25° C. using a MCB1200 magnetic mixer, before the beads were collected on the side of the tube using a magnet and the remaining liquid containing the nucleic acid removed with a pipette, then a second batch of 10 µl of hydroxylapatite-nucleic acid beads prepared as in Example 1 were added to the remaining liquid and mixed for 5 minutes at 25° C. using a MCB1200 magnetic mixer, before the beads were collected on the side of the tube using a magnet and the remaining liquid. containing the purified nucleic acid removed with a pipette and analysed.

EXAMPLE 13

Removing EtBr from a Polymer

It has been found that the positively charged molecule ethidium bromide can be removed from nucleic acids as follows; 10 µl of hydroxylapatite-nucleic acid beads prepared as in Example 1 were added to a mixture of DNA and a weak concentration (1-50 ng/ml) of ethidium bromide and mixed for 5 minutes at 25° C. using a MCB1200 magnetic mixer, before the beads were collected on the side of the tube using a magnet and the remaining liquid containing the ethidium bromide free nucleic acid removed with a pipette.

EXAMPLE 14

Modified RNA

RNA coatings of solid phases can be sensitive to RNase attack and degradation. A simple method to protect such coatings of RNA is to chemically modify the 2-OH groups of the RNA, thus rendering them RNase resistant. Methods and materials for modifying RNA are set out in European patent applications 2000/929665.8 and 2000/929666.6 or alternatively kits are commercially available for this purpose (Stab-MRT Kit, RNAworks, France).

To 10 µl (50 mg/ml) of magnetic hydroxylapatite Type-I (Chemicell, Germany) in a 1.5 ml polypropylene microcentrifuge tube was added 25 µl of water containing 25 µg of the 2'-OH modified homopolymer poly r(A) (Midland Certified Reagent Company, USA) and mixed for 10 minutes at 25° C. using the 0.5 sec. step program of a MCB1200 magnetic mixer (Dexter Magnetics, UK). The beads were collected with the MCB1200 magnet, the liquid removed from the Type-I beads and the beads washed three times with 0.5 ml water each, before finally being resuspended in a final volume of 10 µl water. Alternatively, 2'-OH modified poly r(A) can be replaced with the same amount of 2'-OH modified poly r(U), poly r(C), poly r(G), poly r(A/U) or a natural source of RNA such as total cellular RNA.

EXAMPLE 15

Immobilising Polymer on HPA Surface by Cross-linking

In order to reduce the amount of the nucleic acid or polypeptide coating that leaches away from the solid phase during transport, storage and use of the material, the coating can be cross linked to produce an interlinked 'mesh' coating. Commonly used methods of cross linking include chemical cross linking such as those set out in European patent application 2000/929665.8 and 2000/929666.6. Reagents such as sebacoyl chloride ($ClOC(CH_2)_8COCl$), adipoyl chloride ($ClOC(CH_2)_4COCl$) and glutaryl chloride ($ClOC(CH_2)_3COCl$) can all be used to cross-link the RNA coating together as set out in this application.

To 10 µl (50 mg/ml) of magnetic hydroxylapatite Type-I (Chemicell, Germany) in a 1.5 ml polypropylene microcentrifuge tube was added 25 µl of water containing 25 µg of the homopolymer poly d(A) (Midland Certified Reagent Company, USA) and mixed for 10 minutes at 25° C. using the 0.5 sec. step program of a MCB1200 magnetic mixer (Dexter Magnetics, UK). The beads were collected with the MCB1200 magnet, the liquid removed from the Type-I beads and the beads washed three times with Tetrahydrofuran, before finally being resuspended in a final volume of 100 µl Tetrahydrofuran containing 20% (v/v) sebacoyl, adipoyl or glutaryl chloride. The reaction was allowed to proceed for 1 hr at 25° C. before collection of the coated and cross linked magnetic particles with a magnet and removal of the liquid reagents. The coated and cross linked magnetic particles were then washed three times with 0.5 ml water each, before finally being resuspended in a final volume of 10 µl water. Alternatively, poly r(A) can be replaced with the same amount of poly r(U), poly r(C), poly r(G), poly r(A/U), or a natural source of RNA such as total RNA.

Other cross linking methods for nucleic acids are set out in Current Protocols in Nucleic Acid Chemistry, Chapter 5, Wiley.

EXAMPLE 17

Removing Fluorescently Labelled Nucleotides from a Fluorescently Labelled Probe for Microarray Analysis Unincorporated, free fluorescently labelled nucleotides can be simply removed from fluorescently labelled cDNA prior to hybridisation as follows; A CyScribe™ cDNA labelling kit (Part. No. 6201, Amersham Pharmacia Biosciences, UK) or other DNA labelling kits such as Fluorescein High Prime (Roche Molecular, France), Nick Translation Kit (Vysis Inc, USA), BioProbe Random Primed DNA Labeling Kit (Sigma Aldrich, USA) or Renaissance Random Primer Labeling Kit (PerkinElmer, USA) were used according to the manufacturer's instructions. 10 µl of hydroxylapatite-nucleic acid beads prepared as in Example 1 were added to the labelling reaction and mixed for 5 minutes at 25° C. using a MCB1200 magnetic mixer, before the beads were collected on the side of the tube using a magnet and the remaining liquid containing the nucleotide free labelled DNA probe sample removed with a pipette and used according to standard hybridisation procedures.

EXAMPLE 18

Removing Biotin Labelled Nucleotides from a Biotinylated Probe

The solid phase of the material can also be a nucleic acid, protein or other macromolecule. For example streptavidin can be coated onto a magnetic particle, then covered with a coating of nucleic acid, such prepared particles can be used to remove by affinity binding, undesired small biotinylated molecules such as nucleotides from the desired biotinylated analyte polynucleotide. Without the coating of nucleic acid, the analyte biotinylated nucleic acid will be bound to the streptavidin solid phase and therefore lost. Suitable particles for covalently binding streptavidin include magnetic beads such as M-450, M-450 Epoxy or M-450 Tosylactivated (Dynal, Norway) or it has been found that silica and plastic beads can also retain streptavidin, probably by hydrophobic interactions. Methods to coat magnetic beads with proteins are well known in the art (Wang et al., (1998) Blood 92:756). Alternatively, commercially available streptavidin beads are also available from a number of vendors (Dynabeads M-270 Streptavidin, Dynal, Norway). The surface coating nucleic acid can be applied to the streptavidin coated solid phase most simply by using biotin modified polynucleotides which are simply prepared using a biotinylated nucleotide triphosphate and a DNA polymerase or kinase as found in various kits such as BioPrime DNA Labeling System, (Invitrogen, USA). Coating with the biotinylated nucleic acid should be non-saturating, as determined empirically for the streptavidin so that the streptavidin retains its capacity to bind additional undesired biotinylated nucleotide. The biotinylated surface coating serves to coat the streptavidin and therefore stop the binding of the analyte nucleic acid to it. Samples containing both the undesired contaminating biotinylated nucleotide and the desired analyte nucleic acid are applied to the surface treated solid phases and mixed by gentle agitation for 5-60 minutes at ambient temperature. The solid phase is then removed by any number of methods including filtration, centrifugation or magnetic collection and the desired biotinylated analyte removed by pipetting.

Alternatively, the streptavidin can be coated with a positively charged macromolecule such as biotinylated polyglutamate or poly-aspartate in order to separate a positively charged undesired biotinylated amino acid from the desired biotinylated analyte protein or macromolecule. Proteins can be biotinylated using a number of commercialised kits such as FluoReporter Mini-Biotin-XX Protein Labeling Kit (Molecular probes, USA). Regardless of the charge of the surface coating, its function is to slow down or stop the binding of the desired analyte to the solid phase.

The invention claimed is:

1. A set of materials comprising two separate compositions of matter, wherein:
   a) the first composition of matter is a sample comprising an analyte and an undesired constituent, wherein the analyte is a polynucleotide, and the undesired constituent is selected from a nucleotide, an anionic detergent or a chelator; and
   b) the second composition of matter is a material comprising a composition comprising a solid phase that is coated with polynucleotides at least 20 nucleotides in length, wherein:
      i) the solid phase can bind both the undesired constituent and the analyte;
      ii) the polynucleotide coating covers the exposed surface of the solid phase to an extent that any binding of the solid phase to the analyte is impeded;
      iii) said polynucleotides are attached to said solid phase ionic interactions; and
      iv) the sample and the second material are not in contact with each other.

2. The set of materials according to claim 1, wherein:
   a) more than 90% of the undesired constituent can be bound by the solid phase; and
   b) less than 10% analyte can be bound by the solid phase.

3. The set of materials according to claim 1, wherein the solid phase comprises agarose, acrylamide, polyethylene, polycarbonate, polypropylene, polystyrene, acrylic, quartz, rubber, polyester, polyvinyl chloride, polyurethane, nylon, nitrocellulose, glass, hydroxylapatite, fluorapatite, silica, a metal, a metal salt or a metal oxide.

4. The set of materials according to claim 3, wherein said metal or the metal present in said metal salt or metal oxide is calcium, iron, chromium, gallium, germanium, lithium, magnesium, manganese, palladium, cesium, tungsten, selenium, tin, vanadium, molybdenum, nickel, copper, zinc, aluminum, silver, gold, platinum or lead.

5. The set of materials according to claim 1, wherein the undesired constituent is a chelator.

6. The set of materials according to claim 1, wherein the solid phase further comprises a magnetic component.

7. The set of materials according to claim 6, wherein the solid phase is magnetic hydroxylapatite.

8. The set of materials according to claim 1, wherein the solid phase is in the form of a bead, particle, sheet, gel, powder, filter or membrane.

9. The set of materials according to claim 1, wherein the coating of polynucleotides is attached to the surface of the solid phase by ionic interactions.

10. The set of materials according to claim 9, wherein the solid phase is coated with an oligonucleotide or polynucleotide.

11. The set of materials according to claim 10, wherein the oligonucleotide or polynucleotide is a single, double or triple stranded RNA molecule.

12. The set of materials according to claim 11, wherein the single, double or triple stranded RNA molecule is an RNA homopolymer, in vitro transcribed RNA, total RNA, rRNA, tRNA or mRNA.

13. The set of materials according to claim 10, wherein the oligonucleotide or polynucleotide is a single, double or triple stranded DNA molecule.

14. The set of materials according to claim 13, wherein the single, double or triple stranded DNA molecule is a DNA homopolymer, synthetic DNA, prokaryotic or eukaryotic genomic DNA, phage DNA, viral DNA or mitochondrial DNA.

15. The set of materials according to claim 10, wherein the oligonucleotide or polynucleotide is cross linked.

16. The set of materials according to claim 10, wherein the solid phase comprises magnetic hydroxylapatite and the surface treatment material consists of polynucleotides having at least 20 nucleotides.

17. The set of materials according to claim 16, wherein the surface treatment material consists of polynucleotides having at least 50 nucleotides.

18. The set of materials according to claim 1, wherein said analyte is DNA.

19. The set of materials according to claim 1, wherein said solid phase surface is coated with polynucleotides at a density sufficient to cover the surface in its entirety.

20. A method of binding an undesired constituent to a solid phase comprising mixing the set of materials of claim 1 and allowing said undesired constituent to bind to the coated solid phase.

21. The method according to claim 20, further comprising separating the analyte from said undesired constituent.

22. The set of materials according to claim 1, wherein said undesired constituent is a detergent.

23. The set of materials according to claim 1, wherein said undesired constituent is a nucleotide.

24. The set of materials according to claim 23, wherein said nucleotide is labeled.

25. The set of materials according to claim 23, wherein said nucleotide is unlabeled.

26. The set of materials according to claim 1, wherein said polynucleotides are attached to said solid phase by encapsulation coating.

27. The set of materials according to claim 1, wherein said polynucleotides are attached to said solid phase by adsorption.

28. The set of materials according to claim 1, wherein said polynucleotides are attached to said solid phase by absorption.

29. The set of materials according to claim 1, wherein said polynucleotides are attached to said solid phase by hydrophobic interactions.

30. A set of materials comprising two separate compositions of matter, wherein:
   a) the first composition of matter is a sample comprising an analyte and an undesired constituent, wherein the analyte is a polynucleotide, and the undesired constituent is selected from a nucleotide, an anionic detergent or a chelator; and
   b) the second composition of matter is a solid phase material comprising hydroxylapatite coated with polynucleotides at least 20 nucleotides in length, wherein:
      i) the solid phase material can bind both the undesired constituent and the analyte;
      ii) the polynucleotide coating covers the exposed surface of the solid phase material to an extent that any binding of the solid phase to the analyte is impeded;
      iii) said polynucleotides are attached to said solid phase material by interaction with calcium cations on the surface of said solid phase material; and
      iv) the sample and the second material are not in contact with each other.

31. The set of materials according to claim 30, wherein said undesired constituent is a detergent.

32. The set of materials according to claim 30, wherein said undesired constituent is a chelator.

33. The set of materials according to claim 30, wherein said undesired constituent is a nucleotide.

34. The set of materials according to claim 33, wherein said nucleotide is labeled.

35. The set of materials according to claim 33, wherein said nucleotide is unlabeled.

36. The set of materials according to claim 30, wherein the solid phase material is magnetic hydroxylapatite.

37. The set of materials according to claim 1, wherein said first composition of matter is a sample comprising an analyte and an undesired constituent, wherein the analyte is a polynucleotide, and the undesired constituent is a nucleotide; and
   b) the second composition of matter is a material comprising a composition comprising a solid phase that is coated with polynucleotides at least 20 nucleotides in length, wherein:
      i) the solid phase can bind both the undesired constituent and the analyte;
      ii) the polynucleotide coating covers the exposed surface of the solid phase to an extent that any binding of the solid phase to the analyte is impeded;
      iii) said polynucleotides are attached to said solid phase by ionic interactions; and
      iv) the sample and the second material are not in contact with each other.

\* \* \* \* \*

UNITED STATES PATENT AND TRADEMARK OFFICE
CERTIFICATE OF CORRECTION

| | | |
|---|---|---|
| PATENT NO. | : 7,790,373 B2 | Page 1 of 1 |
| APPLICATION NO. | : 10/565694 | |
| DATED | : September 7, 2010 | |
| INVENTOR(S) | : Goldsborough | |

It is certified that error appears in the above-identified patent and that said Letters Patent is hereby corrected as shown below:

Column 4,
Line 39, "ethidiun bromide" should read --ethidium bromide--.

Signed and Sealed this
Eighteenth Day of January, 2011

David J. Kappos
*Director of the United States Patent and Trademark Office*